US00PP09145P

United States Patent [19]

Glicenstein

[11] Patent Number: Plant 9,145

[45] Date of Patent: May 30, 1995

[54] CHRYSANTHEMUM PLANT NAMED SUNNY LINDA

[75] Inventor: Leon Glicenstein, Salinas, Calif.

[73] Assignee: Yoder Brothers, Inc., Barberton, Ohio

[21] Appl. No.: 155,239

[22] Filed: Nov. 22, 1993

[51] Int. Cl.[6] ..... A01H 5/00

[52] U.S. Cl. ..... Plt./78

[58] Field of Search ..... Plt. 78

[56] References Cited

U.S. PATENT DOCUMENTS 4,616,099 10/1986 Sparkes ..... 47/58

OTHER PUBLICATIONS

Broertjes, et al., 1980, "A mutant of a mutant of a . . . Irradiation of progressive radiation-induced mutants in a mutation breeding programme with *Chrysanthemum morifolium*", Euphytica, 29:526–530.

Gosling, ed., 1979, "The Chrysanthemum Manual–6th edition", The National Chrysanthemum Society, London, Essex Telegraph Press, Ltd., pp. 329–336.

Broertjes, et al., 1978, "Application of Mutation Breeding Methods In the Improvement of Vegetatively Propagated Crops", Elsevier Sci. Pub. Co., New York, pp. 162–175.

Searle, et al., 1968, "Chrysanthemum the Year Round", Blanford Press, London, pp. 27–29, 320–327.

Chan, 1966, "Chrysanthemum and rose mutations induced by X-rays", Am. Soc. Hort. Sci. Proc., pp. 613–620.

Broertjes, 1966, "Mutation breeding of chrysanthemums", Euphytica, 15:156–162.

Dowrick, et al., 1966, "The induction of mutations in Chrysanthemum using X-and gamma radiation", Euphytica, 15:204–210.

*Primary Examiner*—Howard J. Locker

*Attorney, Agent, or Firm*—Foley & Lardner

[57] ABSTRACT

A Chrysanthemum plant named Sunny Linda particularly characterized by its flat capitulum form; decorative capitulum type; yellow ray floret color; diameter across face of capitulum of 51 to 64 mm when fully opened; branching pattern is spreading and prolific, with 7 to 9 breaks after pinch when grown outside under natural daylength in fall flowerings and in 10 cm pots for spring flowerings; natural season flower date of August 16 to 31 when planting rooted cuttings on June 21 to June 23 in Salinas, Calif., and October 2 to 5 when planting rooted cuttings June 15 to 18 in Hightstown, N.J.; flowering response of 48 to 53 days after rooting in no light/no shade programs in spring; plant height of 25 to 30 cm when grown in fall under natural daylength with no growth regulators in New Jersey, and 18 to 20 cm when grown in 10 cm pots in spring with 0 to 2 applications of 2500 ppm B-9 SP; and durable, uniform performance.

1 Drawing Sheet

The present invention comprises a new and distinct cultivar of Chrysanthemum, botanically known as *Dendranthema grandiflora,* and referred to by the cultivar name Sunny Linda.

Sunny Linda, identified as 8133 (86-490D01), is a product of a mutation induction program. The new cultivar was discovered and selected by Leon Glicenstein on Jul. 8, 1991, in a controlled environment in Salinas, Calif. as one flowering plant within a flowering block established as rooted cuttings from stock plants which had been exposed as unrooted cuttings to an X-ray source of 2000 rads in Fort Myers, Fla. on Mar. 6, 1991. The irradiated parent cultivar was the cultivar identified as Linda, disclosed in U.S. Plant Pat. No. 8,294, and described as decorative garden mum with white flower color and a light yellow center of the flower.

The irradiation program resulting in Sunny Linda had as its primary objective the expansion of color ranges of the parent cultivar Linda. The irradiation program comprised irradiating cuttings of the parent cultivar at irradiation levels of 1500, 1750 and 2000 rads. A total of 946 cuttings harvested from a total of 225 irradiated plants were planted on May 13, 1991, May 6, 1991, and May 6, 1991, respectively. Of these, 20 initial selections were made, which selections were then revegetated and reflowered. Three consecutive flowerings resulted in discarding 15 of the original 20 selections on Mar. 19, 1992. Two codes were reselected, which reselections were ultimately discarded on Nov. 10, 1992. The remaining five selections were maintained as PIs (Possible Introductions) and further trialed in Salinas, Calif., Hightstown, N.J. and Leamington, Ontario, Canada, ultimately resulting in the decision to discard four of these codes on Oct. 1, 1992 and to introduce selection 8133 as Sunny Linda.

The first act of asexual reproduction of Sunny Linda was accomplished when vegetative cuttings were taken from the initial selection in September 1991 in a controlled environment in Salinas, Calif., by technicians working under supervision of Leon Glicenstein.

Horticultural examination of controlled flowerings of successive plantings has shown that the unique combination of characteristics as herein disclosed for Sunny Linda are firmly fixed and are retained through successive generations of asexual reproduction.

Sunny Linda has not been observed under all possible environmental conditions. The phenotype may vary significantly with variations in environment such as temperature, light intensity and daylength, without, however, any variation in genotype.

The following observations, measurements and comparisons describe plants grown in controlled open areas in Salinas, Calif., and in Hightstown, N.J. Rooted cuttings were established in soil and maintained outdoors under the natural temperature and daylength prevailing during June through October. Spring flowerings were conducted in Salinas, Calif. under greenhouse conditions which approximate those generally used in commercial greenhouse practice for small pot spring garden mum production.

The following traits have been repeatedly observed and are determined to be basic characteristics of Sunny Linda, which, in combination, distinguish this Chrysanthemum as a new and distinct cultivar:

1. Flat capitulum form.
2. Decorative capitulum type.
3. Yellow ray floret color.
4. Diameter across face of capitulum of 51 to 64 mm when fully opened.
5. Branching pattern is spreading and prolific, with 7 to 9 breaks after pinch when grown outside under natural daylength in fall flowerings and in 10 cm pots for spring flowerings.
6. Natural season flower data of August 16 to 31 when planting rooted cuttings on June 21 to June 23 in Salinas, Calif., and October 2 to 5 when planting rooted cuttings June 15 to 18 in Hightstown, N.J.
7. Flowering response of 48 to 53 days after rooting in no light/no shade programs in spring.
8. Plant height of 25 to 30 cm when grown in fall under natural daylength with no growth regulators in New Jersey, and 18 to 20 cm when grown in 10 cm pots in spring with 0 to 2 applications of 2500 ppm B-9 SP.
9. Durable, uniform performance.

The accompanying photographic drawing is a color photograph of Sunny Linda grown as a pinched garden mum under natural season outside conditions in Salinas, Calif., with the colors being as nearly true as possible with illustrations of this type. Plants were grown outside and dug and transplanted into 15 cm bulb pans at flowering time for photography purposes.

Of the commercial cultivars known to the inventor, the most similar in comparison to Sunny Linda is the parent cultivar Linda. All traits of Sunny Linda are similar to those of Linda, except for the ray floret color. The ray floret color of Sunny Linda is yellow, while the ray floret color of Linda is white with a light yellow center of the flower. In several natural season fall flowering trails Sunny Linda has flowered several days earlier than Linda when grown side by side.

In the following description, color references are made to The Royal Horticultural Society Colour Chart. The color values were determined on plant material grown as a pinched garden mum grown under natural season outside conditions in Salinas, Calif. on Aug. 16, 1993.

Classification:

*Botanical.*—*Dendranthema grandiflora* cv Sunny Linda.

*Commercial.*—Flat decorative spray pot mum and garden mum.

INFLORESCENCE

A. Capitulum:

*Form.*—Flat.

*Type.*—Decorative.

*Diameter across face.*—51 to 64 mm when fully opened.

B. Corolla of ray florets:

*Color (general tonality from a distance of three meters).*—Yellow.

*Color (upper surface).*—6A to 6B.

*Color (under surface).*—6C.

*Shape.*—Cross section concave, longitudinal section of outer ray florets convex. Petal tips slightly pointed.

C. Corolla of disc florets:

*Color (mature).*—14B.

*Color (immature).*—144C.

D. Reproductive organs:

*Androecium.*—Present on disc florets only, no to very scant pollen.

*Gynoecium.*—Present on both ray and disc florets.

PLANT

A. General appearance:

*Height.*—25 to 30 cm when grown in fall under natural daylength with no growth regulators in New Jersey, and 18 to 20 cm when grown in 10 cm pots in spring with 0 to 2 applications of 2500 ppm B-9 SP.

*Branching pattern.*—Spreading and prolific, with 7 to 9 breaks after pinch when grown outside under natural daylength in fall flowerings and in 10 cm pots for spring flowerings.

B. Foliage:

*Color (upper surface).*—147A.

*Color (under surface).*—147B.

*Shape.*—Relatively small, moderately deep lobes, and slightly serrated.

I claim:

1. A new and distinct Chrysanthemum plant named Sunny Linda, as described and illustrated.

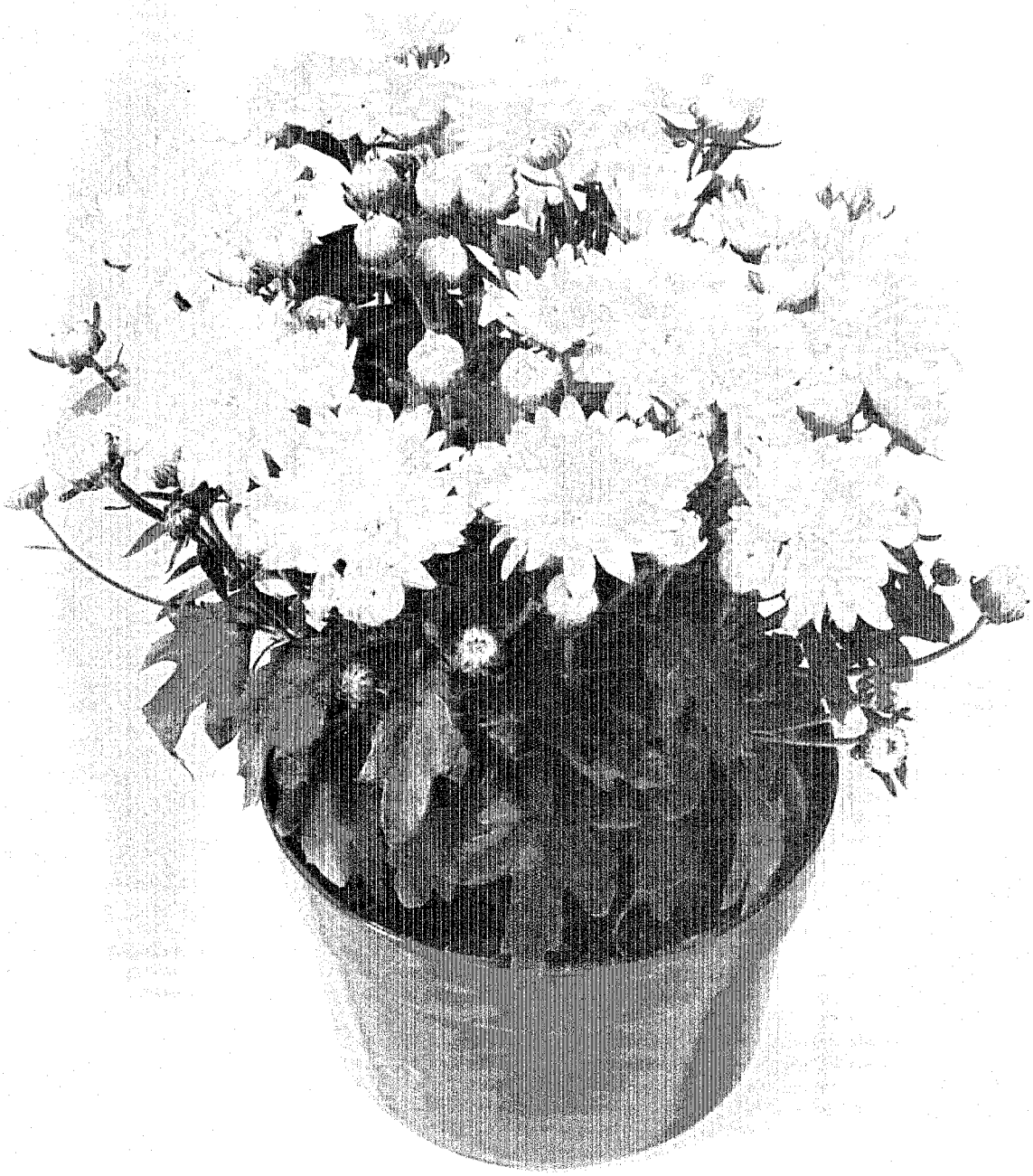

* * * * *